US011083859B2

(12) United States Patent
Börner

(10) Patent No.: US 11,083,859 B2
(45) Date of Patent: Aug. 10, 2021

(54) RESPIRATOR AND METHOD FOR DETERMINING A FRESH GAS FLOW

(71) Applicant: Dräger Medical GmbH, Lübeck (DE)

(72) Inventor: Jonas Börner, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1327 days.

(21) Appl. No.: 14/706,197

(22) Filed: May 7, 2015

(65) Prior Publication Data
US 2015/0320950 A1 Nov. 12, 2015

(30) Foreign Application Priority Data

May 8, 2014 (DE) .................. 10 2014 006 780

(51) Int. Cl.
A61M 16/00 (2006.01)
A61M 16/06 (2006.01)
A61M 16/20 (2006.01)
A61M 16/10 (2006.01)
(Continued)

(52) U.S. Cl.
CPC .... *A61M 16/0003* (2014.02); *A61M 16/0057* (2013.01); *A61M 16/024* (2017.08); *A61M 16/06* (2013.01); *A61M 16/104* (2013.01); *A61M 16/20* (2013.01); *A61B 5/087* (2013.01); *A61B 5/7203* (2013.01); *A61B 2562/0247* (2013.01); *A61M 16/208* (2013.01); *A61M 2016/003* (2013.01);
(Continued)

(58) Field of Classification Search
CPC .......... A61M 16/00–16/0003; A61M 16/0045; A61M 16/0051–16/0084; A61M 2016/0015–2016/0018; A61M 2016/0027–2016/003; A61M 2016/0033–2016/0042; A61M 2205/3331–2205/3334; A61M 2205/3341; A61M 2205/3351–2205/3355; A61B 2562/0247
See application file for complete search history.

(56) References Cited

U.S. PATENT DOCUMENTS 6,945,123 B1 9/2005 Kuehl et al.
2006/0283450 A1 12/2006 Shissler et al.
2014/0345609 A1* 11/2014 Whitcher ............ C01B 13/0259
128/202.26

FOREIGN PATENT DOCUMENTS

DE 101 61 057 A1 7/2003
WO 2011/147438 A1 12/2011

* cited by examiner

Primary Examiner — Rachel T Sippel
(74) Attorney, Agent, or Firm — McGlew and Tuttle, P.C.

(57) ABSTRACT

A respirator (1) includes a fresh gas port (23, 25, 27) for connecting a fresh gas supply, a gas outlet (3) for connecting a supply line for a patient, an absolute pressure sensor (21) and a data processor (37). The gas outlet and the fresh gas port are fluidically connected via an inhalation branch (17) that is connected to the absolute pressure sensor. The fresh gas port has an adjusting valve (31), to set gas flow from the fresh gas supply to the inhalation branch, and a differential pressure sensor (33). The differential pressure sensor determines a differential pressure in the fresh gas port between the inhalation branch and the adjusting valve. The data processor receives and records the absolute pressure measured and the differential pressure to determine a fresh gas flow through the fresh gas port. A method for determining a fresh gas flow is also shown and described.

14 Claims, 1 Drawing Sheet

(51) Int. Cl.
*A61B 5/00* (2006.01)
*A61B 5/087* (2006.01)
(52) U.S. Cl.
CPC ............... *A61M 2016/0027* (2013.01); *A61M 2205/3331* (2013.01); *A61M 2205/50* (2013.01); *A61M 2205/502* (2013.01)

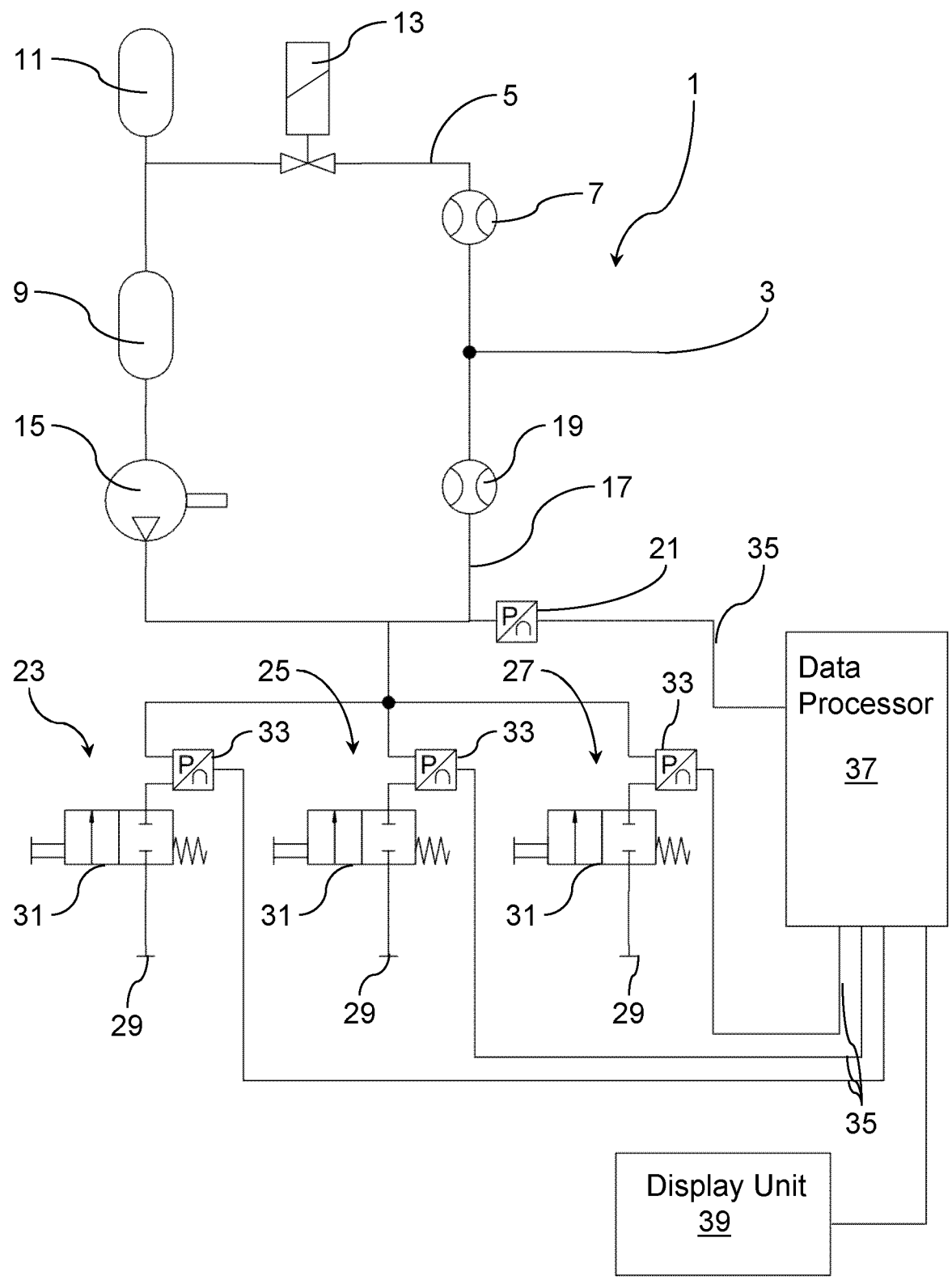

RESPIRATOR AND METHOD FOR DETERMINING A FRESH GAS FLOW

CROSS REFERENCE TO RELATED APPLICATIONS

This application claims the benefit of priority under 35 U.S.C. § 119 of German Patent Application DE 10 2014 006 780.7 filed May 8, 2014, the entire contents of which are incorporated herein by reference.

FIELD OF THE INVENTION

The present invention pertains to a respirator with a fresh gas port, a gas outlet, an absolute pressure sensor and a data processor, wherein the gas outlet is set up to connect a supply line for a patient and is fluidically connected with the fresh gas port via an inhalation branch, wherein the absolute pressure sensor is arranged and set up to measure an absolute pressure in the inhalation branch, and wherein the fresh gas port is set up for connecting a fresh gas supply and comprises an adjusting valve and a differential pressure sensor, wherein a gas flow from the fresh gas supply to the inhalation branch can be set via the adjusting valve and the differential pressure sensor is arranged and set up to measure a differential pressure in the fresh gas port between the inhalation branch and the adjusting valve, as well as to a method for determining a fresh gas flow.

BACKGROUND OF THE INVENTION

To respirate (ventilate) a patient with a respirator (also known as a ventilator) or even with an anesthesia apparatus, the patient is connected with a gas outlet of the respirator via a supply line. The air exhaled by the patient is collected by an exhalation branch of the device and processed by the respirator. Among other things, carbon dioxide is removed in this case from the air and previously consumed components of the breathing gas, for example, oxygen and gaseous anesthetics, are fed from a fresh gas supply via a fresh gas port. The processed breathing air is made available again to the patient via an inhalation branch. The fresh gases are fed via one or more fresh gas ports, which are connected with the gas outlet via the inhalation branch. The fresh gas ports are set up for connecting fresh gas supplies, for example, in the form of gas cylinders, a central gas supply or even a redundant gas supply, with which automatic switching is possible between a central gas supply and a gas cylinder.

Each fresh gas port comprises an adjusting valve and a differential pressure sensor. The admission of fresh gas is set with the adjusting valve, which may be an electronically or manually controlled adjusting valve. The differential pressure sensor is intended for measuring or determining the differential pressure between the adjusting valve and the inhalation branch. A flow of the fresh gas—the fresh gas flow—into the respirator, which is used as the basis for setting the adjusting valve, can, in turn, be determined from the measured or determined differential pressure. If the adjusting valve is controlled or regulated electronically, the determined fresh gas flow can be used directly to regulate or control the adjusting valve such that a predetermined fresh gas flow or desired flow is reached. However, the adjusting valve often needs to be regulated manually, for example, for regulatory reasons. The determined fresh gas flow is visualized for this on a display, and a human operator sets the adjusting valve such that the determined fresh gas flow corresponds to the desired flow.

However, it has proved to be difficult in practice to set the adjusting valves, because the differential pressure measured by the differential pressure sensor is not constant or changes at least only slowly, and it is also impossible to display a constant fresh gas flow for the setting. In case of pressure changes, for example, when a valve in the exhalation branch closes and/or the patient's breathing phase changes, there are brief compensation processes, which become noticeable by pressure waves in the respirator. These pressure waves lead to a short-term fluctuation of the differential pressure, which is determined by the differential pressure sensor. These fluctuations are imposed as narrow-band interferences on the fresh gas flows determined and make it difficult to set the adjusting valves correctly. A simple averaging over time of the fresh gas flows determined or of the differential pressures determined would be suitable, in principle, for filtering out the narrow-band interferences, but an averaging could make it even more difficult to set the fresh gas flow, because changes in the set fresh gas flow lead to a change in the determined fresh gas flow with a marked time delay only.

This problem can be solved or at least markedly mitigated, in principle, by arranging the fresh gas ports in the respirator as far away from the gas outlet as possible. The longer the section that the breathing-induced pressure waves must travel before they reach the differential pressure sensor, the weaker is the interference. The drawback of this arrangement is, however, the fact that it takes considerably longer for a change in the setting of the adjusting valves to lead to a change in the composition of the breathing gas that is made available to the patient at the gas outlet. To make it possible to respond in a short time, the fresh gas ports are therefore preferably arranged at the shortest distance possible from the gas outlet. However, the differential pressure sensor and hence the determined fresh gas flow are also subject to especially great interferences there.

SUMMARY OF THE INVENTION

In view of the problems known from the state of the art, an object of the present invention is to provide a respirator and a method in which a fresh gas flow can be determined as free from breathing-induced, narrow-band interferences as possible.

In a first aspect, the basic object of the present invention is accomplished by a respirator, in which the data processor is connected with the absolute pressure sensor and the differential pressure sensor in order to receive and record the absolute pressure measured by the absolute pressure sensor at a plurality of times and the differential pressure measured by the differential pressure sensor at a plurality of times. The data processor is set up (configured) to determine a fresh gas flow through the fresh gas port at a defined time from the differential pressure measured at the defined time, the absolute pressure measured at the defined time and one or more absolute pressures, which were measured at times located in time before the defined time.

The respirator according to the present invention, which may also be an anesthesia apparatus, comprises a gas outlet and a fresh gas port, which are connected via an inhalation branch. An inhalation branch is defined as a part of a respirator through which a breathing gas flows before it is made available at the gas outlet to a patient, who is connected with the gas outlet, for example, via a breathing mask or a supply line having a different design. An absolute pressure sensor, with which the absolute pressure in the inhalation branch, i.e., the pressure of the breathing gas in the inhalation branch, can be measured or determined, is arranged in or at the inhalation branch. An absolute pressure is defined here as a pressure of a gas in relation to a constant or only slowly changing reference pressure, for example, vacuum or ambient pressure.

The absolute pressure is preferably measured against vacuum, because the absolute pressure thus measured can be used directly as a reference variable for the fresh gas flow measurement.

The fresh gas port is set up to be connected with a fresh gas supply, for example, in the form of a gas cylinder, a central gas supply or even a redundant gas supply. A redundant gas supply is a common port for a central gas supply and a gas cylinder, which is set up such that fresh gas is taken from the gas cylinder only when the pressure in the central gas supply drops below a needed pressure. The fresh gas port comprises, furthermore, an adjusting valve, with which the fresh gas flow from a fresh gas supply connected to the fresh gas port into the respirator can be set. The adjusting valve may be, for example, a mechanical adjusting valve, which must be set manually by a user. A user must set a desired fresh gas flow manually in this case. However, it is also conceivable that the adjusting valve is set electronically by the data processor and a user only enters a desired fresh gas flow into the data processor and the data processor performs the setting of the adjusting valve. In addition, a differential pressure sensor is set up between the adjusting valve of the fresh gas port and the inhalation branch in order to measure the differential pressure between the adjusting valve and the inhalation branch. In a preferred exemplary embodiment, the differential pressure sensor is a metering orifice, at which the pressure difference, i.e., the differential pressure over the metering orifice is proportional to the second power of the mass flow and the volume flow.

The data processor, for example, a conventional PC or an integrated circuit, is connected with the differential pressure sensor and the absolute pressure sensor, the sensors or even pressure sensors. The connection may take place, for example, via data lines, via which the digital measured values are transmitted from the sensors. As an alternative, the connection may also take place via analog measuring lines, via which a current or voltage signal corresponding to the measured pressures is transmitted. The differential and absolute pressures measured by the sensors at defined times are received and recorded by the data processor. For example, the data processor can record the differential and absolute pressures measured at 10-msec intervals. Especially in case of an analog transmission between the sensors and the data processor, but also in case of digital transmission, it is possible to define the defined time at which a differential pressure or an absolute pressure was measured as the time at which the differential pressure or absolute pressure was received by the data processor.

The data processor is set up to determine a fresh gas flow through the fresh gas port at a defined time. The data processor uses for this first the differential pressure measured at the defined time. In addition, the determination of the differential pressure also includes the absolute pressure determined at the defined time as well as at least one additional absolute pressure, which was measured at a time that preceded the defined time.

The present invention makes it advantageously possible to also include in the determination of the fresh gas flow, besides the differential pressure, at least two absolute pressure measurements, at least one of which was carried out chronologically prior to the defined time. The influence of breath-induced interferences can thus be taken into account in the determination of the fresh gas flow. These interferences propagate as pressure waves from the gas outlet of the respirator in the direction of the fresh gas port through the inhalation branch. Before the pressure waves reach the differential pressure sensor and can interfere with the measurement of the differential pressure, they inevitably first pass through the absolute pressure sensor and affect the measured absolute pressure before the measured differential pressure is affected. The subsequently occurring effect on the differential pressure can thus be estimated from the influence of the pressure waves on the measured absolute pressure and this influence can be taken into account in the determination of the fresh gas flow. The fresh gas flow thus determined can be displayed via a display device to a user of the respirator, who would like to set the fresh gas flow manually via a mechanical adjusting valve. The displayed fresh gas flow is advantageously free from narrow-band, breathing-induced interferences, as a result of which the setting of the desired fresh gas flow is markedly facilitated for the user. Even if the adjusting valve is set electronically, the determination of a corrected fresh gas flow is advantageous, because the time needed for the correct setting of the adjusting valve is markedly reduced.

In a preferred embodiment, the respirator has at least one additional fresh gas port, wherein the at least one additional fresh gas port is connected with the gas outlet via the inhalation branch and for connecting a fresh gas supply, wherein the at least one additional fresh gas port comprises an adjusting valve and a differential pressure sensor, wherein a gas flow from a fresh gas supply connected to an additional fresh gas port to the inhalation branch can be set via the adjusting valve, and the differential pressure sensor is arranged and set up to measure a differential pressure in the at least one additional fresh gas port between the adjusting valve and the inhalation branch, wherein the data processor is connected with the differential pressure sensor of the at least one additional fresh gas port in order to receive and record the differential pressure measured by the differential pressure sensor at a plurality of times, and wherein the data processor is set up to determine a fresh gas flow through the at least one additional fresh gas port at the defined time from the differential pressure measured by the differential pressure sensor of the at least one additional fresh gas port at the defined time, from the absolute pressure measured at the defined time and from one or more absolute pressures, which was/were measured at times chronologically preceding the defined time.

In the preferred embodiment, the device has at least one additional fresh gas port, which is arranged in parallel to the first fresh gas port and has the same design. The data processor can advantageously determine a fresh gas flow at a defined time for these fresh gas ports as well from the differential pressure measured by the differential pressure sensor of the respective fresh gas port at the defined time and from the already known absolute pressures. Besides the advantages known for a single fresh gas port, the additional advantage arising here is that the absolute pressure, once measured, can be used to correct a plurality of differential pressures. It is preferred here that the data processor is set up to determine a mean value of the absolute pressure from the absolute pressures, which were measured at a plurality of times preceding the defined time, and to additionally determine the fresh gas flow or the fresh gas flows from the mean values of the absolute pressure, which were determined for such times, at which an absolute pressure, which is included in the determination of the fresh gas flow or the fresh gas flows, was measured. A sliding mean value of the absolute value is formed in the preferred embodiment, for example, over the last 20 sec before a defined time. The data processor continuously records for this the absolute pressures measured by the absolute pressure sensor and stores the values for as long as necessary.

Furthermore, it is preferred that the data processor is set up to determine the fresh gas flow or the fresh gas flows from the differences of the absolute pressures and the mean values of the absolute pressure, which were measured and determined at the same times. Brief fluctuations of the absolute pressure, which propagate in the respirator in the form of pressure waves, can be advantageously determined by difference formation.

Furthermore, it is preferred that the data processor is set up to determine the fresh gas flow or the fresh gas flows from a corrected differential pressure or corrected differential pressures, wherein the corrected differential pressure or corrected differential pressures is/are determined by means of a transfer function from the measured differential pressure or measured differential pressures and the absolute pressures included in the determination of the respective fresh gas flow. The known relationship between the differential pressure and the fresh gas flow can thus be advantageously used without changes by correcting the measured differential pressure by means of the measured absolute pressures. This correction is preferably performed by means of a transfer function, for example, a transfer function for time-discrete systems.

The transfer function preferably has the following form:

$$dP_{corr}(z) = dP(z) - \frac{b_1 \tilde{P}(z) + b_2 \tilde{P}(z-1) + b_3 \tilde{P}(z-2)}{a_1 \tilde{P}(z) + a_2 \tilde{P}(z-1) + a_3 \tilde{P}(z-2)},$$

wherein z is the defined time, dP(z) is the differential pressure at the time z, $dP_{corr}(z)$ is the corrected differential pressure at the time z, $\tilde{P}(z)$ is the difference from the absolute pressure measured for the time z and the mean value of the absolute pressure determined for the time z, z−1 and z−2 being times preceding the defined time z, and $a_1$, $a_2$, $a_3$, $b_1$, $b_2$ and $b_3$ are coefficients. A discrete time signal is used in the preferred embodiment and the absolute pressures measured at the two directly preceding times are also used besides the absolute pressure measured for the defined time for correcting the differential pressure at a defined time.

The coefficients $a_1$, $a_2$, $a_3$, $b_1$, $b_2$ and $b_3$ are determined in such a way that the differential pressures and the absolute pressure are recorded for different times in case of a typical pressure surge during the inhalation at constant fresh gas flow, i.e., with the adjusting valves set permanently and hence with a permanently preset differential pressure. The needed values are determined from the measured and recorded values. Since the individual differential pressure values are permanently preset by the respective constant fresh gas flow, the coefficients can be subsequently determined, for example, with the least error square method.

The preferred transfer function can be calculated rapidly and makes it possible to correct the differential pressure and hence also the determined fresh gas flow with sufficiently high accuracy to correct the interferences generated in the differential pressure by the changing breathing phases of a patient connected to the respirator.

In a preferred embodiment, the adjusting valve or adjusting valves is/are mechanical adjusting valves, which are adjusted manually by a user of the respirator, and the data processor comprises a display device, on which the fresh gas flow determined before or the fresh gas flows determined before can be displayed for a user of the respirator.

In another aspect, the object according to the present invention is accomplished by a method for determining a fresh gas flow at a defined time through a fresh gas port of a respirator from a differential pressure and a plurality of absolute pressures, which were measured at different times, wherein the differential pressure is measured between an adjusting valve of the fresh gas port, with which the fresh gas flow through the fresh gas port is set, and an inhalation branch of the respirator, wherein the fresh gas port is connected, at least in some sections, with a gas outlet to the port of a supply line for a patient via the inhalation branch, wherein the absolute pressure in the inhalation branch is measured and wherein the fresh gas flow is determined at a defined time from the differential pressure measured for the defined time, from the absolute pressure measured for the defined time and at least one absolute pressure that was measured for a time preceding the defined time.

A mean value of the absolute pressure is preferably determined from the absolute pressures that were measured at a plurality of times preceding the defined time for each time at which an absolute value that was taken into account in the determination of the fresh gas flow was measured, and the fresh gas flow or fresh gas flows are additionally determined from the mean values of the absolute pressure, which were determined for such times at which an absolute pressure, which is included in the determination of the fresh gas flow or fresh gas flows, was measured.

The fresh gas flow is preferably determined from the differences of the absolute pressures and the mean values of the absolute pressure, which were measured or determined for the same times.

The fresh gas flow is preferably determined from a corrected differential pressure, wherein the corrected differential pressure is determined from the measured differential pressure and the absolute pressures included in the determination of the fresh gas flow. The transfer function is preferably in the form of $$dP_{corr}(z) = dP(z) - \frac{b_1 \tilde{P}(z) + b_2 \tilde{P}(z-1) + b_3 \tilde{P}(z-2)}{a_1 \tilde{P}(z) + a_2 \tilde{P}(z-1) + a_3 \tilde{P}(z-2)},$$

wherein z is the defined time, dP(z) is the differential pressure at the time z, $dP_{corr}(z)$ is the corrected differential pressure at the time z, $\tilde{P}(z)$ is the difference from the absolute pressure measured for the time z and the mean value of the absolute pressure determined for the time z, z−1 and z−2 being times preceding the defined time z, and $a_1$, $a_2$, $a_3$, $b_1$, $b_2$ and $b_3$ are coefficients.

The embodiments of the method according to the present invention are advantageous for the same reasons as the proposed embodiments of the respirator according to the present invention, which have mutually corresponding method and device features.

The present invention will be explained below on the basis of a drawing, which shows only a preferred exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred the preferred exemplary embodiment of the invention is illustrated.

BRIEF DESCRIPTION OF THE DRAWINGS

FIG. 1 is a schematic view showing an exemplary embodiment of a respirator according to the present invention.

DESCRIPTION OF THE PREFERRED EMBODIMENTS

Referring to the drawings, an exemplary embodiment of a respirator 1 according to the present invention will be described with reference to FIG. 1. The respirator 1 shown in FIG. 1 is an anesthesia apparatus with a closed breathing circuit. However, the present invention is by no means limited to respirators 1 with a closed breathing circuit, but it may also be used in respirators 1 that have a half-open breathing circuit.

A patient, who shall be respirated with the respirator 1, is connected to the respirator 1 via a supply line, for example, a breathing mask, at the gas outlet 3. Breathing air exhaled by the patient flows through the gas outlet 3 into an exhalation branch 5, which comprises a flow sensor 7. The flow sensor 7 measures the volume or mass flow of the breathing air exhaled by the patient. The exhaled breathing air is sent from the exhalation branch 5 through a breathing lime cartridge 9, which binds carbon dioxide contained in the breathing air. A respiration bag 11 and an exhalation adjusting valve 13 are arranged between the exhalation branch 5 and the breathing lime cartridge 9. Breathing air can be stored intermediately in the respiration bag 11 before it is processed and fed again to the patient. The exhalation adjusting valve 13 always closes whenever the patient is inhaling and thus prevents used breathing air that has not yet been processed from being inhaled again by the patient. Furthermore, the respirator 1 comprises a blower 15 to generate the pressure needed for the respiration in the processed breathing air.

The processed breathing air is subsequently fed again to the gas outlet 3 and, via this outlet, to a patient connected with the gas outlet 3 via a supply line. An additional flow sensor 19, with which the volume or mass flow of the processed breathing air inhaled by the patient can be measured, is arranged in the inhalation branch 17. In addition, an absolute pressure sensor 21, with which an absolute pressure of the breathing gas in the inhalation branch 17 can be measured, is arranged along the inhalation branch 17. An absolute pressure is defined here as the pressure of the breathing gas in the inhalation branch 17 relative to a vacuum or an only slowly changing reference pressure, e.g., the ambient pressure.

Three fresh gas ports 23, 25, 27 are arranged between the blower 15 and the inhalation branch 17. The three fresh gas ports 23, 25, 27 have an identical design. The same reference numbers are therefore used for identically named components of the fresh gas ports 23, 24, 27, and only one of the fresh gas ports 23, 25, 27, which is representative of the other fresh gas ports 23, 25, 27, is described here in detail.

Each of the fresh gas ports 23, 25, 27 has a connection component 29 for connecting a fresh gas supply, for example, in the form of a gas cylinder, a central gas supply or a redundant gas supply. A mechanical adjusting valve 31, with which a user of the respirator 1 can set the gas flow from a connected fresh gas supply into the respirator 1 manually, is arranged between the connection element 29 and the inhalation branch 17. To make it possible to monitor the fresh gas flow from the fresh gas supply into the respirator 1 and, more specifically, into the inhalation branch 17, a differential pressure sensor 33 in the form of a metering orifice is additionally arranged in each of the fresh gas ports 23, 25, 27 between the adjusting valve 31 and the inhalation branch 17. The differential pressure sensor 33 measures a differential pressure, which can also be called pressure difference. The differential pressure is proportional to the second power of the mass or volume flow of the fresh gas—the fresh gas flow—through the differential pressure sensor 33 and thus from the fresh gas supply into the respirator 1.

It had been found problematic in the state of the art that the differential pressure measured by a differential pressure sensor 33 and the determined fresh gas flow from it are interfered with by the constant pressure change in the inhalation branch 17 and the exhalation branch 5 of the respirator 1. In other words, the differential pressure sensor 33 also measures a narrow-band interference, which is generated, for example, by the breathing rhythm of a patient or the closing and opening of the exhalation adjusting valve 13, besides the differential pressure, which corresponds to the actual fresh gas flow. However, this interference leads to a constant fluctuation of the fresh gas flow, which is displayed to a user, who attempts to set a fresh gas flow by means of the adjusting valve 31, and correct setting is thus extremely difficult.

To counteract this interference, provisions are made in the present invention for connecting the absolute pressure sensor 21 and the differential pressure sensor 33 via data lines 35 with a data processor 37. The data transmission between the sensors 21, 33 may be digital, but also analog, i.e., the sensors 21, 33 may transmit the measured pressures either as digital data to the data processor 37, or they may transmit a voltage or current signal analogous to the measured pressure to the data processor 37, which converts this analog signal into a digital value. The data processor 37 records the absolute and differential pressures received and assigns them to a plurality of times. The plurality of times may be either the times at which the measurement of the respective pressure was, indeed, performed, or times at which a measured pressure was received by the data processor 37. In any case, there is a discrete time signal, so that a measured absolute pressure can, as a rule, be assigned to a time and a measured differential pressure can be assigned to each differential pressure sensor 33.

For a defined time, usually the closest preceding time, the data processor 37 determines a fresh gas flow through the fresh gas port 23, 25, 27 from the differential pressure, which was measured by the differential pressure sensor 33 for the defined time, from the absolute pressure measured by the absolute pressure sensor 21 for the defined time and from at least one absolute pressure measured at a chronologically preceding time. A corrected differential pressure, from which a corrected fresh gas flow can be calculated, is formed first for this. The corrected differential pressure is determined from the measured differential pressure, the measured absolute pressures and sliding means values of the absolute pressure by means of a transfer function. The transfer function is $$dP_{corr}(z) = dP(z) - \frac{b_1 \tilde{P}(z) + b_2 \tilde{P}(z-1) + b_3 \tilde{P}(z-2)}{a_1 \tilde{P}(z) + a_2 \tilde{P}(z-1) + a_3 \tilde{P}(z-2)},$$

where z is the defined time, dP(z) is the differential pressure measured by the differential pressure sensor 33 at the time z, dPcorr(z) is the corrected differential pressure at the time z, P̃(z) is the difference from the absolute pressure measured by the absolute pressure sensor 21 for the time z and the mean value of the absolute pressure determined for the time z, z−1 and z−2 are times chronologically preceding the defined time z, and $a_1$, $a_2$, $a_3$, $b_1$, $b_2$ and $b_3$ are coefficients. The data processor 37 determines the fresh gas flow through the respective fresh gas port 23, 25, 27 from the corrected differential pressure in the manner known from the state of the art. The determined fresh gas flow is displayed on a display device 39 for a user of the respirator 1, so that the user can set the respective fresh gas flow to the desired value on the manual adjusting valves 31 without difficulties.

In other words, an exemplary embodiment of a method according to the present invention is carried out with the exemplary embodiment of a respirator 1 according to the present invention. The absolute pressure is measured first for this at a plurality of times by the absolute pressure sensor 21 in the inhalation branch 17 of the respirator 1. In addition, a differential pressure is measured by a differential pressure sensor 33 in each of the three fresh gas ports 23, 25, 27 at a plurality of times. For further processing, the measured pressures are transmitted via data lines 35 to the data processor 37, which determines a fresh gas flow from the absolute pressure measured at the defined time and from an absolute pressure, which was measured at a time preceding the defined time.

The determination is carried out by first determining a sliding mean value of the absolute pressure for a time at which an absolute pressure that shall be taken into account in the determination of the fresh gas flow was measured, for example, over the last 20 sec before this time. The difference of the absolute pressure and the sliding mean value of the absolute value, which mean value was determined for the given time, is then taken into account for each time in the further course of the determination of the fresh gas flow. These differences are processed together with the differential pressure measured for the defined time in a transfer function in order to determine a corrected differential pressure from this. The corrected differential pressure is obtained according to the formula:

$$dP_{corr}(z) = dP(z) - \frac{b_1 \tilde{P}(z) + b_2 \tilde{P}(z-1) + b_3 \tilde{P}(z-2)}{a_1 \tilde{P}(z) + a_2 \tilde{P}(z-1) + a_3 \tilde{P}(z-2)},$$

where z is the defined time, dP(z) is the differential pressure measured by the differential pressure sensor 33 at the time z, dPcorr(z) is the corrected differential pressure at the time z, P̃(z) is the difference from the absolute pressure measured by the absolute pressure sensor 21 for the time z and the mean value of the absolute pressure determined for the time z, z−1 and z−2 are times chronologically preceding the defined time z, and $a_1$, $a_2$, $a_3$, $b_1$, $b_2$ and $b_3$ are coefficients. A corrected differential pressure, which is largely free from short-term interferences, which propagate through the inhalation branch 17 as pressure waves towards the fresh gas ports 23, 25, 27, is subsequently determined from the corrected differential pressure. The corrected fresh gas flow is displayed for a user on the display device 39.

The exemplary embodiment of the respirator 1 according to the present invention and also the exemplary embodiment of the method according to the present invention, which is carried out by the respirator 1, are advantageous for various reasons. Firstly, they make it possible to determine a fresh gas flow through the fresh gas ports 23, 25, 27, which is largely free from narrow-band interferences, which are generated by the changing breathing pressures of a patient. Since the changing breathing pressures propagate in the form of pressure waves through the consultation direction 1 and especially the inhalation branch 17, these first pass through the absolute pressure sensor 21 before they are detected by the differential pressure sensor 33, so that the pressure measured by the absolute pressure sensor can be advantageously used to correct a pressure measured by the differential pressure sensor 33.

While specific embodiments of the invention have been shown and described in detail to illustrate the application of the principles of the invention, it will be understood that the invention may be embodied otherwise without departing from such principles.

Appendix:

LIST OF REFERENCE NUMBERS

1 Respirator
3 Gas outlet
5 Exhalation branch
7 Flow sensor
9 Breathing lime cartridge
11 Respiration bag
13 Exhalation adjusting valve
15 Blower
17 Inhalation branch
19 Flow sensor
21 Absolute pressure sensor
23 Fresh gas port
25 Fresh gas port
27 Fresh gas port
29 Connection element
31 Adjusting valve
33 Differential pressure sensor
35 Data line
37 Data processor
39 Display unit

What is claimed is:

1. A respirator comprising:
a fresh gas port for connecting a fresh gas supply, the fresh gas port comprising an adjusting valve and a differential pressure sensor;
an inhalation branch, a gas flow from the fresh gas supply to the inhalation branch being set via the adjusting valve, the differential pressure sensor being arranged and configured to measure a differential pressure in the fresh gas port between the inhalation branch and the adjusting valve;
a gas outlet for connecting a supply line for a patient, the gas outlet being connected fluidically with the fresh gas port via the inhalation branch;
an absolute pressure sensor arranged to measure an absolute pressure in the inhalation branch;
a data processor connected with the absolute pressure sensor and connected with the differential pressure sensor to receive and record the absolute pressure measured by the absolute pressure sensor at a plurality of times and to receive and record the differential pressure measured by the differential pressure sensor at a plurality of times, wherein the data processor is configured to determine a fresh gas flow through the fresh gas port at a defined time from the differential pressure measured at the defined time, from the absolute pressure measured at the defined time and from one or more absolute pressures measured at times chronologically preceding the defined time.

2. A respirator in accordance with claim 1, further comprising at least one additional fresh gas port connected with the gas outlet via the inhalation branch and configured for connecting a fresh gas supply, the at least one additional fresh gas port comprising an adjusting valve and a differential pressure sensor, wherein:
- a gas flow from a fresh gas supply connected to the at least one additional fresh gas port to the inhalation branch is set by the at least one additional fresh gas port adjusting valve;
- the at least one additional fresh gas port differential pressure sensor is arranged and set up to measure a differential pressure in the at least one additional fresh gas port between the at least one additional fresh gas port adjusting valve and the inhalation branch;
- the data processor is connected with the at least one additional fresh gas port differential pressure sensor to receive and record the differential pressure measured by the at least one additional fresh gas port differential pressure sensor at a plurality of times; and
- the data processor is configured to determine a fresh gas flow through the at least one additional fresh gas port from the differential pressure measured at the defined time by the at least one additional fresh gas port differential pressure sensor, from the absolute pressure determined at the defined time and from one or more absolute pressures measured at times chronologically preceding the defined time.

3. A respirator in accordance with claim 1, wherein:
- the data processor is configured to determine a mean value of the absolute pressure for each time at which an absolute pressure is measured from absolute pressures measured at a plurality of times chronologically preceding the defined time; and
- the data processor is configured to determine the fresh gas flow or fresh gas flows from the mean values of the absolute pressure, which mean values are determined for such times, at which an absolute pressure was measured, which is included in the determination of the fresh gas flow or fresh gas flows.

4. A respirator in accordance with claim 3, wherein the data processor is configured to determine the fresh gas flow or fresh gas flows from differences of the absolute pressures and of the mean values of the absolute pressure measured and determined for the same times.

5. A respirator in accordance with claim 1, wherein the data processor is configured to determine a corrected fresh gas flow from a corrected differential pressure, wherein the corrected differential pressure is determined by a transfer function from the measured differential pressure and the absolute pressures influencing the determination of the fresh gas flow.

6. A respirator in accordance with claim 5, wherein the transfer function has the form of $$dP_{corr}(z) = dP(z) - \frac{b_1 \tilde{P}(z) + b_2 \tilde{P}(z-1) + b_3 \tilde{P}(z-2)}{a_1 \tilde{P}(z) + a_2 \tilde{P}(z-1) + a_3 \tilde{P}(z-2)},$$

wherein z is the defined time, dP(z) is the differential pressure at the time z, $dP_{corr}(z)$ is the corrected differential pressure at the time z, $\tilde{P}(z)$ is the difference from the absolute pressure measured for the time z and the mean value of the absolute pressure determined for the time z, z−1 and z−2 being times preceding the defined time z, and $a_1$, $a_2$, $a_3$, $b_1$, $b_2$ and $b_3$ are coefficients.

7. A respirator in accordance with claim 2, wherein the data processor is configured to determine a corrected fresh gas flow or corrected fresh gas flows from a corrected differential pressure or corrected differential pressures, wherein the corrected differential pressure or corrected differential pressures is/are determined by a transfer function from the measured differential pressure or measured differential pressures and the absolute pressures influencing the determination of the respective fresh gas flow.

8. A respirator in accordance with claim 1, wherein:
- the adjusting valve is a mechanical adjusting valve, adjusted manually by a user of the respirator; and
- the data processor comprises a display device, on which the previously determined fresh gas flow or previously determined fresh gas flows can be displayed for the user of the respirator.

9. A respirator in accordance with claim 2, wherein:
- the adjusting valves are each mechanical adjusting valves, adjusted manually by a user of the respirator; and
- the data processor comprises a display device, on which the previously determined fresh gas flow or previously determined fresh gas flows can be displayed for the user of the respirator.

10. A method for determining a fresh gas flow at a defined time through a fresh gas port of a respirator from a differential pressure and a plurality of absolute pressures, which are measured at different times, the method comprising:
- providing the fresh gas port of the respirator with an adjusting valve with which a fresh gas flow through the fresh gas port is set;
- connecting the fresh gas port, at least in some sections, with a respirator gas outlet via an inhalation branch for connecting a supply line for a patient;
- measuring a differential pressure between the adjusting valve of the fresh gas port and an inhalation branch of the respirator,
- measuring an absolute pressure in the inhalation branch; and
- determining a fresh gas flow for the defined time from the differential pressure measured at the defined time, from the absolute pressure measured for the defined time and from at least one absolute pressure measured for a time chronologically preceding the defined time.

11. A method in accordance with claim 10, wherein:
- a mean value of the absolute pressure is determined from the absolute pressures that were measured at a plurality of times preceding the defined time for each time at which an absolute pressure taken into account in the determination of the fresh gas flow was measured; and
- the fresh gas flow is additionally determined from the mean values of the absolute pressure, which mean values were determined for such times at which an absolute pressure, which is included in the determination of the fresh gas flow or fresh gas flows, was measured.

12. A method in accordance with claim 11, wherein the fresh gas flow is determined from the differences of the absolute pressures and the mean values of the absolute pressure, which were measured or determined for the same times.

13. A method in accordance with claim 10, wherein a corrected fresh gas flow is determined from a corrected differential pressure, wherein the corrected differential pressure is determined by means of a transfer function from the measured differential pressure and the absolute pressures that are included in the determination of the fresh gas flow.

14. A method in accordance with claim 13, wherein the transfer function has the form of $$dP_{corr}(z) = dP(z) - \frac{b_1 \tilde{P}(z) + b_2 \tilde{P}(z-1) + b_3 \tilde{P}(z-2)}{a_1 \tilde{P}(z) + a_2 \tilde{P}(z-1) + a_3 \tilde{P}(z-2)},$$

wherein z is the defined time, dP(z) is the differential pressure at the time z, $dP_{corr}(z)$ is the corrected differential pressure at the time z, $\tilde{P}(z)$ is the difference from the absolute pressure measured for the time z and the mean value of the absolute pressure determined for the time z, z−1 and z−2 being times preceding the defined time z, and $a_1$, $a_2$, $a_3$, $b_1$, $b_2$ and $b_3$ are coefficients.

* * * * *